(12) United States Patent
Chinchoy et al.

(10) Patent No.: US 7,715,917 B2
(45) Date of Patent: May 11, 2010

(54) METHOD AND APPARATUS FOR DETERMINING AN EFFICACIOUS ATRIOVENTRICULAR DELAY INTERVAL

(75) Inventors: Edward Chinchoy, Golden Valley, MN (US); Nirav V. Sheth, Coon Rapids, MN (US); Kathryn E. Hilpisch, St. Paul, MN (US); Thomas J. Mullen, Andover, MN (US); John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 811 days.

(21) Appl. No.: 11/004,543

(22) Filed: Dec. 3, 2004

(65) Prior Publication Data

US 2005/0149137 A1 Jul. 7, 2005

Related U.S. Application Data

(60) Provisional application No. 60/527,261, filed on Dec. 3, 2003.

(51) Int. Cl.
*A61N 1/00* (2006.01)
(52) U.S. Cl. ...................................................... 607/25
(58) Field of Classification Search .................. 607/25, 607/27, 9, 14
See application file for complete search history.

(56) References Cited

U.S. PATENT DOCUMENTS

| | | | |
|---|---|---|---|
| 6,070,101 A | 5/2000 | Struble et al. | |
| 6,122,545 A * | 9/2000 | Struble et al. | ................... 607/9 |
| 6,360,127 B1 | 3/2002 | Ding et al. | |
| 6,473,645 B1 | 10/2002 | Levine | |
| 6,522,923 B1 * | 2/2003 | Turcott | ........................ 607/27 |
| 6,542,775 B2 | 4/2003 | Ding et al. | |
| 6,704,600 B2 * | 3/2004 | Daum | ......................... 607/30 |
| 6,751,504 B2 * | 6/2004 | Fishler | ........................ 607/25 |
| 6,885,889 B2 | 4/2005 | Chinchoy | |
| 7,024,242 B2 * | 4/2006 | Lu | ............................... 607/14 |
| 7,212,857 B2 * | 5/2007 | Weinberg et al. | ............... 607/9 |
| 2003/0018363 A1 | 1/2003 | Ding et al. | |
| 2004/0172078 A1 | 9/2004 | Chinchoy | |
| 2005/0027320 A1 | 2/2005 | Nehls et al. | |

(Continued)

OTHER PUBLICATIONS

Wang et al., "Atrial Electromechanical Sequence in Normal Subjects and Patients with DDD Pacemakers", Oct. 1995, British Heart Journal, 74(4), 403-407.*

(Continued)

*Primary Examiner*—George Manuel
(74) *Attorney, Agent, or Firm*—Stephen W. Bauer

(57) ABSTRACT

Determining an optimal atrioventricular interval is of interest for proper delivery of cardiac resynchronization therapy. Although device optimization is gradually and more frequently being performed through a referral process with which the patient undergoes an echocardiographic optimization, the decision of whether to optimize or not is still generally reserved for the implanting physician. Recent abstracts have suggested a formulaic approach for setting A-V interval based on intrinsic electrical sensing, that may possess considerable appeal to clinicians versus a patient average nominal A-V setting of 100 ms. The present invention presents a methods of setting nominal device settings based on entering patient cardiac demographics to determine what A-V setting may be appropriate. The data is based on retrospective analysis of the MIRACLE trial to determine what major factors determined baseline A-V settings.

16 Claims, 4 Drawing Sheets

U.S. PATENT DOCUMENTS

2005/0209648 A1    9/2005   Burnes et al.

OTHER PUBLICATIONS

Wish et al., "Importance of Left Atrial Timing in the Programming of Dual-Chamber Pacemakers", Sep. 1987, The American Journal of Cardiology, 60(7), 566-571.*

Chirife et al., "Automatic Beat-to-Beat Left Heart AV Normalization: Is It Possible?", Nov. 2003, Pacing and Clinical Electrophysiology, 26(11), 2103-10.*

Kass et al., "Improved Left Ventricular Mechanics from Acute VDD Pacing in Patients with Dilated Cardiomyopathy and Ventricular Conduction Delay", 1999, Circulation, 99, 1567-1573.*

Kolb et al., "Assessment of the Optimal Atrioventricular Delay in Patients with Dual Chamber Pacemakers using Impedance Cardiography and Doppler Echocardiography", 1999, Journal of Clinical and Basic Cardiology, 2, 237-240.*

Bohm et al., "Prolonged PR Interval despite a Programmed Short Sensed AV Delay: the Role of Intra-Atrial Conduction Time", 2002, Europace, 4, 329-331.*

Chirife et al., "Automatic Beat-to-Beat Left Heart AV Normalization: Is It Possible?," Pace, vol. 26; Nov. 2003, pp. 2103-2110.

* cited by examiner

METHOD AND APPARATUS FOR DETERMINING AN EFFICACIOUS ATRIOVENTRICULAR DELAY INTERVAL

CROSS REFERENCE TO RELATED APPLICATIONS

The present non-provisional U.S. patent application claims the benefit of the filing of provisional U.S. patent application Ser. No. 60/527,261 filed 3 Dec. 2003 and having the same title as the present document, the contents of said provisional application are hereby incorporated herein in their entirety.

This application also relates to and hereby incorporates by reference the contents of three non-provisional U.S. patent applications; namely, application Ser. No. 10/376,981 filed 28 Feb. 2003 entitled "METHOD AND APPARATUS FOR ASSESSING LEFT VENTRICULAR FUNCTION AND OPTIMIZING CARDIAC PACING INTERVALS BASED ON LEFT VENTRICULAR WALL MOTION;" application Ser. No. 10/377,207 filed 28 Feb. 2003 which received a Notice of Allowance mailed 5 Nov. 2004 and is entitled "METHOD AND APPARATUS FOR OPTIMIZING CARDIAC RESYNCHRONIZATION THERAPY BASED ON LEFT VENTRICULAR ACCELERATION;" application Ser. No. 10/803,570 filed 17 Mar. 2004 entitled "APPARATUS AND METHODS OF ENERGY EFFICIENT, ATRIAL-BASED BI-VENTRICULAR FUSION-PACING;" and application Ser. No. 10/631,551 filed 30 Jul. 2003 entitled "METHOD OF OPTIMIZING CARDIAC RESYNCHRONIZATION THERAPY USING SENSOR SIGNALS OF SEPTAL WALL MOTION."

FIELD OF THE INVENTION

The present invention relates to the field of cardiac therapy. In particular, the present invention provides methods and apparatus for optimizing an atrioventricular (A-V) interval based on measuring or obtaining one or more physiologic parameters of a patient. The parameters may be obtained using echocardiographic equipment and the like to enhance cardiac therapy delivery, such as a dual chamber pacing therapy and cardiac resynchronization therapy (CRT), among others.

BACKGROUND OF THE INVENTION

Those skilled in the art of diagnosing cardiac ailments have long understood that certain patients, in particular heart failure (HF) patients, suffer uncoordinated mechanical activity wherein the myocardial depolarization and contraction of the atria and ventricles (i.e., right and left) occur in an uncoordinated fashion. Such uncoordinated motion can cause a decrease in stroke volume and/or cardiac output (CO), among other detrimental effects. Recently a variety of techniques have been proposed and practiced for minimizing such uncoordinated motion.

These prior art techniques for minimizing uncoordinated myocardial motion include CRT optimization. One known way to attempt to optimize CRT delivery involves Doppler echocardiographic imaging of ventricular contractions while adjusting interventricular pacing stimulus delivery (i.e., V-V timing). The optimized V-V timing is the interventricular timing that produces the least amount of visibly perceptible dyssynchrony. For successful CRT delivery, the A-V intervals typically are programmed to a magnitude less than the intrinsic atrial-to-ventricular (P-R) interval for a given subject to help ensure bi-ventricular CRT delivery.

An apparatus for delivering CRT includes implantable pulse generator (IPG) with or without high-energy cardioversion/defibrillation therapy capability. An IPG adapted for CRT delivery typically includes three medical electrical leads coupled to myocardial tissue. A first lead typically coupled to the right atrium, a second lead typically coupled to the right ventricle, and a third lead typically coupled to the left ventricle (often via the coronary sinus or great vein). That is, the third lead couples to a location on the free wall of the left ventricle.

Thus, as is known in the art, based at least in part on acute echocardiographic measurement an IPG configured for CRT delivery provides only a limited ability to adjust operative A-V and to a slightly greater degree, V-V intervals. Thus, a need exists in the art for appropriately optimizing electrical cardiac pacing stimulus delivery between the atria and the left ventricle (LV) and/or the right ventricle (RV) in an effort to enhance hemodynamics and other benefits of optimized pacing therapy delivery. When successfully and optimally delivered, certain pacing therapies, such as bi-ventricular CRT, are known to increase CO and may, over time, cause a phenomenon known in the art as "reverse remodeling" of the LV and RV (and/or other beneficial) physiologic changes to the patient's heart.

SUMMARY OF THE INVENTION

The present invention addresses the above described needs by providing means for predicting appropriately timed electrical stimulation of one or both ventricular chambers based on inter-atrial delay and/or characteristics (measured or estimated) of the left ventricular (LV) chamber (e.g., filling characteristics, end-diastolic volume or "LVEDV," end-systolic volume or "LVESV," etc.). The present invention provides for quickly and easily optimizing the atrio-ventricular (A-V) pacing intervals to enhance cardiac resynchronization therapy (CRT) delivery, among other advantages.

Although some practitioners optimize the A-V interval in all of their patients following their reception of a CRT device, the majority of practices send their patient for optimization only if they do not clinically respond to the therapy with a nominal device setting. A major issue that remains is that of reimbursement for the optimization procedures, since in the U.S. echocardiographic optimizations are typically only reimbursed for needed A-V optimization following a three-month (90-day) post-implant time-frame. Additionally, the inventive approach presented herein complements the practice wherein patients are initially screened using echocardiography to determine if they would respond to CRT (presence of mechanical dyssynchrony). During the same echocardiography session, the inter-atrial mechanical delay and LV volume measurements (or estimates) can readily be utilized to program A-V timing for a CRT device following implant.

One feature of the present invention provides an algorithmic approach to determining which patients may benefit from a programmed A-V interval different than a nominal setting (e.g., other than 100 ms), and provides a suggested A-V interval for these patients. A premise behind the invention is an assumption that a patient has an A-V of 100 ms (the average in the MIRACLE trial). Then, by adding or subtracting from that nominal, assumed value—based on current or recently obtained patient cardiac information (e.g., dimensions, inter-atrial delays, etc.) computation (or look-up) of a corrected, operative A-V interval results.

By way of background, the MIRACLE trial data was acquired in blinded fashion in which patients were individually optimized based on maximizing trans-mitral filling. The final histogram of the programmed A-V delays for the entire population resembles a Normal distribution centered at an A-V interval of 100 ms. The standard deviation of the A-V delay was 20 ms. Due in part to measurement uncertainties, the inventors posit that alteration of an A-V interval by 20 ms or less has minimal impact on patient outcome or clinical response, although refining, or tuning, operative A-V intervals by less than 20 ms is considered within the metes and bounds of the present invention. That is, considerable debate exists regarding the importance of A-V intervals, with one extreme of the debate essentially believing in leaving the device settings at a nominal setting (e.g., 100 ms), and the other extreme of the debate believing that periodic automatic A-V interval adjustment is necessary to account for rest and elevated cardiac states. From retrospective analysis of the MIRACLE and MIRACLE ICD data, 66% of patients were set at 100+/−20 ms (mean +/−1 std. dev.). A relevant question therefore becomes whether patients at the extremes can be identified and pacing interval timing programmed more appropriately. The approach of setting the A-V timing by placing patients into discrete "bins" of A-V settings may be of clinical importance versus a nominal A-V=100 ms approach. Based on retrospective data analysis of the MIRACLE trial database, LV size and inter-atrial delays were major factors in determining the final optimal A-V timing interval. Patients with long inter-atrial mechanical delays had significantly longer A-V delays. Patients with smaller LV dimensions at baseline had significantly longer A-V delays.

The algorithm operates using data regarding incidence (and duration) of inter-atrial delays (mechanical or electrical), estimate of relative LV size, and optionally filling characteristics of the atrial and/or ventricular chambers. The algorithm can be used to calculate an operative A-V delay interval based on an original nominal setting (e.g., setting of 80 ms, 90 ms, 100 ms, 110 ms, etc.) and either adding or subtracting increments of A-V timing based on the physiologic information collected for a given patient. Alternatively, the operative A-V delay interval can be generated iteratively. In its simplest form, a constant amount could be added or subtracted from the nominal setting if one or more of the parameters of interest puts the patient in the upper or lower quartile of cardiac performance.

In addition, in a more advanced version of the algorithm according to the present invention, a linear or higher order formula can be employed to compute the amount of shortening or lengthening of the A-V interval based on the extent (or magnitude) of ventricular size or inter-atrial delay. These two measures and others can be employed in combination and need not be sequentially implemented. Such use could include multiparametric equations or more simply for example, a multidimensional so-called "lookup table" (LUT) or other data structure capable of correlating discrete parameters in which an optimal A-V interval (or adjustment thereof) is listed or "mapped" for each combination of the parameters (e.g., inter-atrial delay, ventricular size, chamber filling time, etc.). Such a LUT can be used to correlate discrete heart rate (or ranges of heart rate) to further refine, or tune, the operative A-V delay interval. Thus implemented the algorithm can be embodied in software on a programmer and prompt the clinician or user for echocardiographic- or electrical-derived data relating to the inter- or intra-atrial delay, LV dimensions (e.g., LVEDV, LVESV, etc.). This data would then be processed by a processor running the program to generate an optimal A-V interval based on a model derived from a physiologically similar patient population.

In one embodiment, one generalized technique according to the present invention utilizes baseline echocardiographic data (or any baseline physiologic data) to predict optimal device programming based on a known model derived from a specific patient population, such a clinical trial (e.g., the MIRACLE trial, MIRACLE ICD trial).

In one form of the present invention, an inter-atrial mechanical delay is measured automatically by electrode pairs operatively coupled to an implantable medical device (e.g., P-wave duration from a far field ECG, intra-atrial conduction delay if two atrial leads available) the device then calculates a suggested A-V interval based on the detected inter-atrial delay. According to this form of the invention, continuous or interative A-V interval tuning can be performed while a patient performs activities of daily living (ADL) such as sleeping, sustained physical exertion, driving, etc. With respect to measuring inter-atrial delay a right atrial (RA) lead and a LV lead disposed through the coronary sinus with at least one electrode adjacent the left atria (LA) can be used to sample and adjust A-V interval timing based on essentially real-time data acquisition.

In one form of the invention, a properly-timed single ventricular pacing stimulus produces bi-ventricular synchrony (sometimes called "fusion-based CRT delivery"). Depending at least in part upon the conduction status of a patient, such fusion-based pacing may require what was termed pre-excitation of one ventricle (e.g., the LV) as further described in the co-pending application Ser. No. 10/803,570 to Burnes and Mullen, cross-referenced above and incorporated by reference in its entirety herein.

Thus, the present invention provides novel methods and apparatus implemented to minimize uncoordinated cardiac motion, among other advantages.

With respect to the closed-loop CRT optimization methods and apparatus, in addition to detecting (diagnosing) cardiac mechanical dysfunction using echocardiographic techniques and using data that correlates LVEDV, LVESV, filling characteristics and/or inter-atrial delay with A-V interval provides automatically optimized, dynamically-adjustable CRT pacing modalities. In essence, one basic embodiment of the present invention provides A-V interval timing to maximize the benefits afforded by chronic CRT delivery.

DETAILED DESCRIPTION OF THE INVENTION

As indicated above, the present invention is directed toward providing a method and apparatus for optimizing ventricular function and selecting cardiac pacing intervals for the purposes of restoring ventricular synchrony based on inter- and/or intra-atrial delay, ventricular filling characteristics and/or physiologic dimensions of one or both ventricles. The present invention is useful in optimizing atrial-ventricular, inter-atrial and inter-ventricular pacing intervals during cardiac resynchronization therapy (CRT) used for treating heart failure. The present invention is also useful in selecting pacing parameters used during temporary pacing applied for treating post-operative uncoordinated cardiac chamber (e.g., atrial and/or ventricular) motion. As such, the present invention may be embodied in an implantable cardiac pacing system including a dual chamber or multichamber pacemaker and associated set of medical electrical leads. Alternatively, the present invention may be embodied in a temporary pacing system including an external pacing device with associated temporary pacing leads.

Figure 1:
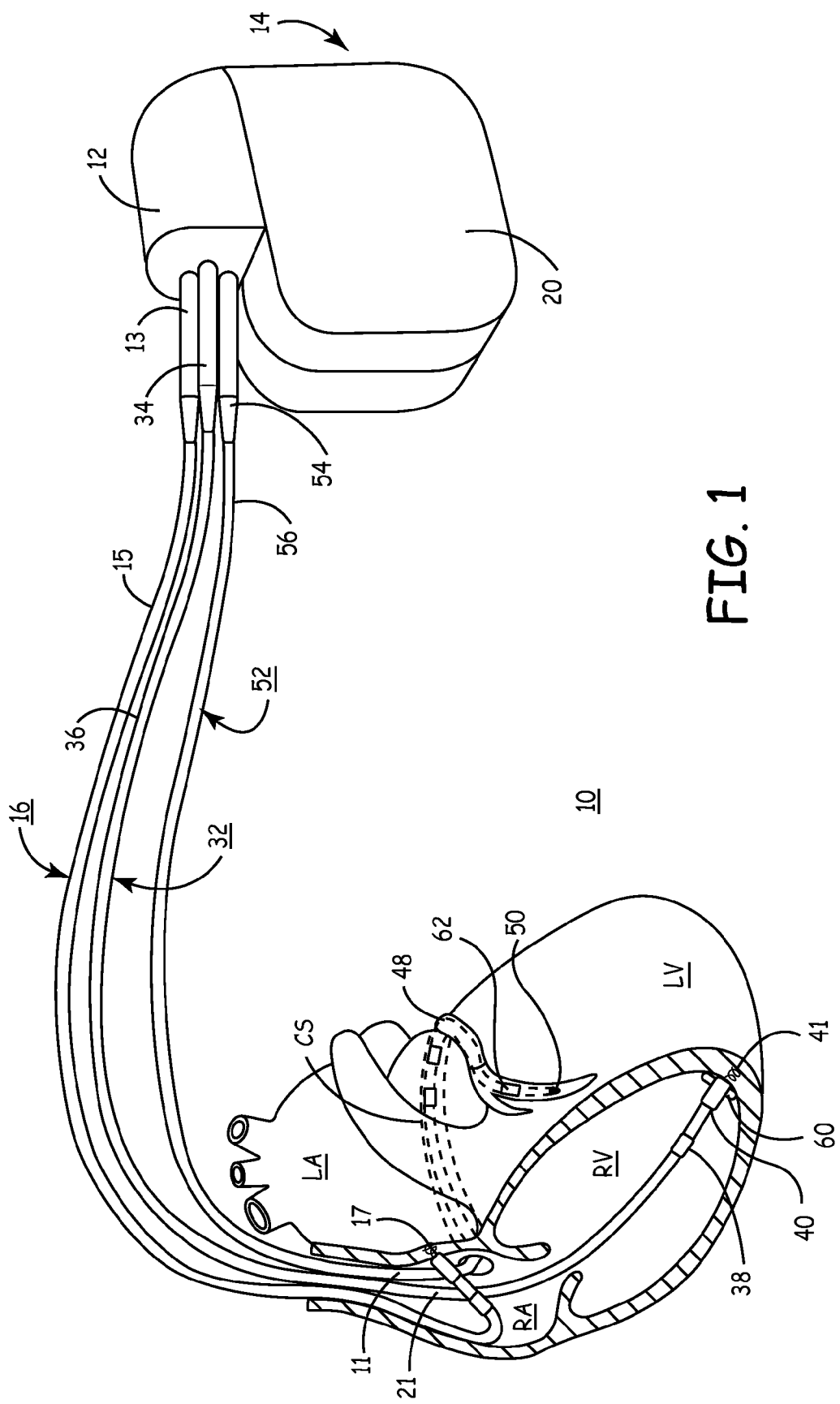
FIG. 1 depicts an exemplary implantable, multi-chamber cardiac pacemaker coupled to a patient's heart via transvenous endocardial leads.

FIG. 1 depicts an exemplary implantable, multi-chamber cardiac pacemaker 14 in which the present invention may be implemented. The multi-chamber pacemaker 14 is provided for restoring ventricular synchrony by delivering pacing pulses to one or more heart chambers as needed to control the heart activation sequence. The pacemaker 14 is shown in communication with a patient's heart 10 by way of three leads 16, 32, 52. The heart 10 is shown in a partially cut-away view illustrating the upper heart chambers, the right atrium (RA) and left atrium (LA) and septal wall (SW) disposed therebetween, and the lower heart chambers, the right ventricle (RV) and left ventricle (LV) and the septal wall (SW) disposed therebetween, and the coronary sinus (CS) extending from the opening in the right atrium laterally around the atria to form the great cardiac vein 48 including branches thereof.

The pacemaker 14, also referred to herein from time to time as an implantable pulse generator (IPG) or an implantable cardioverter-defibrillator (ICD), is implanted subcutaneously in a patient's body between the skin and the ribs. Three transvenous-endocardial leads 16,32,52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The attachment mechanism may be active or passive as is known in the art and as may be later developed. A helix or tined lead may be used as is known in the art, to adapt the distal end of a lead for relatively permanent fixation to myocardial tissue. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 17 and proximal ring RA pace/sense electrode 21 provided for achieving RA pacing and sensing of RA electrogram (EGM) signals.

In accordance with a triple chamber embodiment of the present invention, a coronary sinus lead 52 capable of stimulating the left ventricle is preferably of a relatively small size and diameter such that it may be passed through the coronary sinus and entering a vessel branching from the great cardiac vein and able to be steered to a left ventricular pacing site.

The depicted positions of the leads 16,32,52 and electrodes 38,40,48,62 shown in FIG. 1 in or about the right and left heart chambers are approximate and merely exemplary. Furthermore, it is recognized that alternative leads and pace/sense electrodes that are adapted for placement at pacing or sensing sites on or in or relative to the RA, LA, RV and LV may be used in conjunction with the present invention, including leads having an optional tined member 60 disposed near the distal end portion to enhance passive fixation.

Bipolar, endocardial RV lead 32 passes through the RA into the RV where its distal ring and tip RV pace/sense electrodes 38,40 are adapted for fixation to myocardial tissue by a distal attachment mechanism 41 (and/or by optional tined member 60). The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals.

In the illustrated embodiment of a triple chamber IPG capable of delivering CRT, a unipolar or bipolar or multipolar endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a cardiac vein branching from the great cardiac vein 48.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

Figure 2:
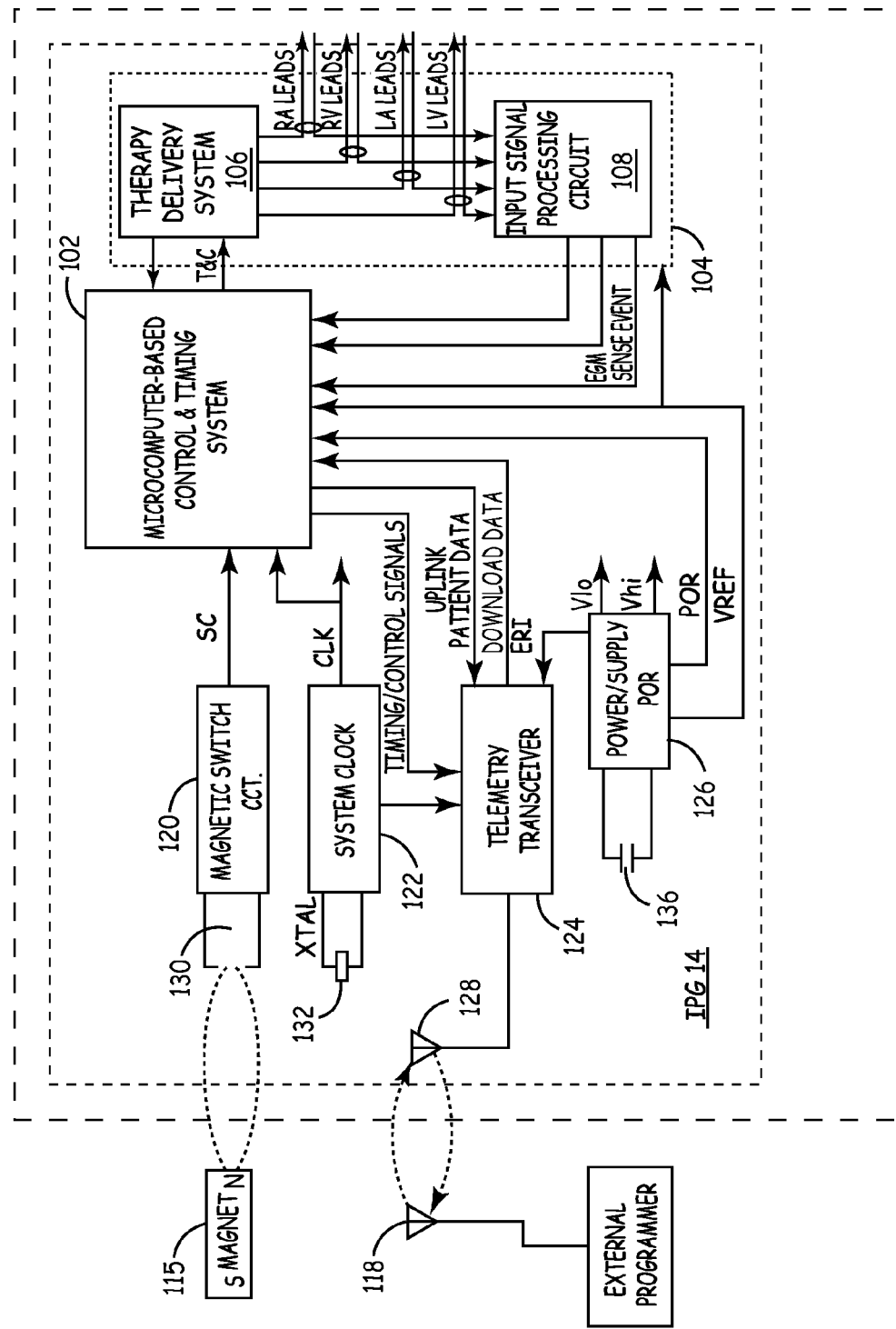
FIG. 2 is a schematic block diagram of the multi-chamber pacemaker of FIG. 1 capable of delivering a resynchronization therapy.

FIG. 2 is a schematic block diagram of an exemplary multi-chamber IPG 14, such as that shown in FIG. 1, that provides delivery of a resynchronization therapy and is capable of processing atrial and/or ventricular signal inputs. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize depolarization of chambers of a patient's heart. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A-A), atrial-ventricular (A-V), and ventricular-ventricular (V-V) intervals.

Physiologic input signal processing circuit 108 is provided for receiving cardiac electrogram (EGM) signals for determining a patient's heart rhythm. Physiologic input signal processing circuit 108 additionally can receive signals related to intra- or inter-atrial delay and processes these signals and provides signal data to control and timing system 102 for further signal analysis and/or storage. For purposes of illustration of the possible uses of the invention, a set of lead connections are depicted for making electrical connections between the therapy delivery system 106 and the input signal processing circuit 108 and sets of pace/sense electrodes located in operative relation to the RA, LA, RV and/or LV.

Control and timing system 102 controls the delivery of bi-atrial, bi-ventricular, or multi-chamber cardiac pacing pulses at selected intervals intended to improve heart chamber synchrony. The initial delivery of pacing pulses by IPG 14 may be programmed to nominal settings or provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable pacing intervals while a patient is ambulatory is preferably based on intra-, inter-atrial delay and/or based upon clinical evidence of ventricular filling characteristics or dimensions of ventricular chamber (i.e., chamber volume) as described herein.

The therapy delivery system 106 can optionally be configured to include circuitry for delivering cardioversion/defibrillation therapy in addition to cardiac pacing pulses for controlling a patient's heart rhythm. Accordingly, as previously mentioned medical electrical leads in communication with the patient's heart can also advantageously include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber pacemaker circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, wall motion signals, and/or relating to device operating history or other sensed physiologic parameters for uplink telemetry transmission upon receipt of a retrieval or interrogation instruction via a downlink telemetry transmission. Criteria for triggering data storage can be programmed via down linked instructions and parameter values. Physiologic data, including septal wall motion data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM data (and data derived therefrom), as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sensed events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of P-waves and R-waves, respectively, and providing atrial sense or ventricular sense event signals to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect. The operative A-V intervals for pacing pulse delivery can vary based on heart rate, sensed level activity (e.g., via a piezoelectric crystal, accelerometer, etc.), detected inter-atrial delay, filling characteristics and/or measured ventricular chamber volume.

Figure 3:
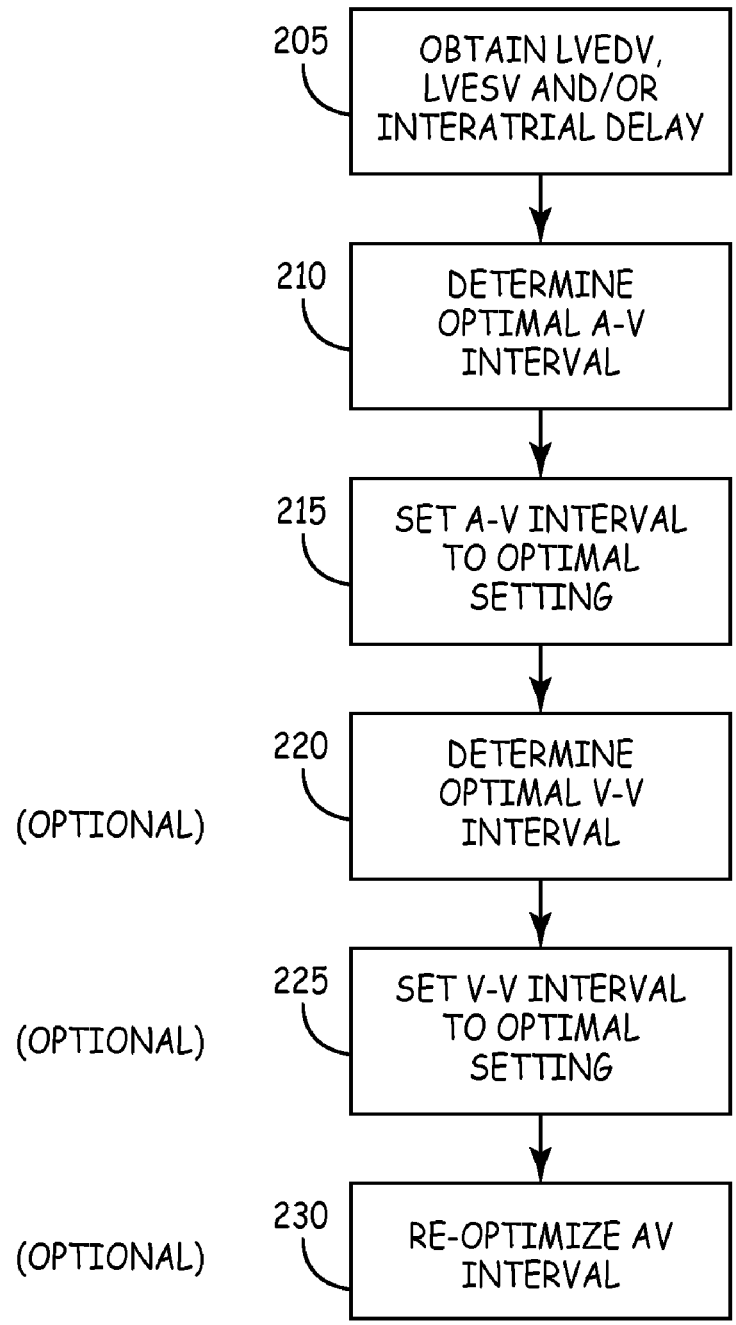
FIG. 3 is a flow chart providing an overview of a method for optimizing cardiac pacing intervals.

FIG. 3 is a flow chart providing an overview of a method for optimizing cardiac pacing intervals according to the present invention. Method 200 begins at step 205, wherein LVEDV, LVESV, filling characteristics and/or measured intra-atrial delay (e.g., measured via ECG, or electrogram—EGM, or using Doppler ultrasound, or mechanically monitored or detected). As is known in the art, these values are readily obtained using known echocardiographic techniques. At step 210, an optimal A-V interval is determined based upon the values obtained in step 205. Depending on the dual chamber or multichamber pacing system being used, a right A-V interval or a left A-V interval or both may be determined. For the embodiment shown in FIG. 1, an optimal RA to LV interval is determined. However, in other embodiments, the left atrial-left ventricular interval is optimized based on the value obtained in step 205 to ensure optimal filling of the LV. At step 215, the A-V interval is automatically adjusted to the optimal A-V interval determined at step 210.

Optionally, at step 220 the optimal V-V interval is determined for bi-ventricular or atrio-biventricular pacing modes. A method for optimizing the V-V interval can be used that relies upon accelerometer sensors coupled to the LV or the ventricular septum and the like (as described and depicted in the co-pending applications incorporated hereinabove). At optional step 225, the V-V interval is automatically adjusted to the optimal V-V interval determined at step 220. After adjusting the V-V interval, an optional step 230 may be performed to re-optimize the A-V interval. Verification of the provisionally determined optimal A-V interval is made by re-determining the optimal A-V interval during biventricular pacing at the newly optimized V-V interval. The A-V interval may be re-adjusted accordingly if a different A-V interval is identified as being optimal during pacing at the optimal V-V interval.

Figure 4:
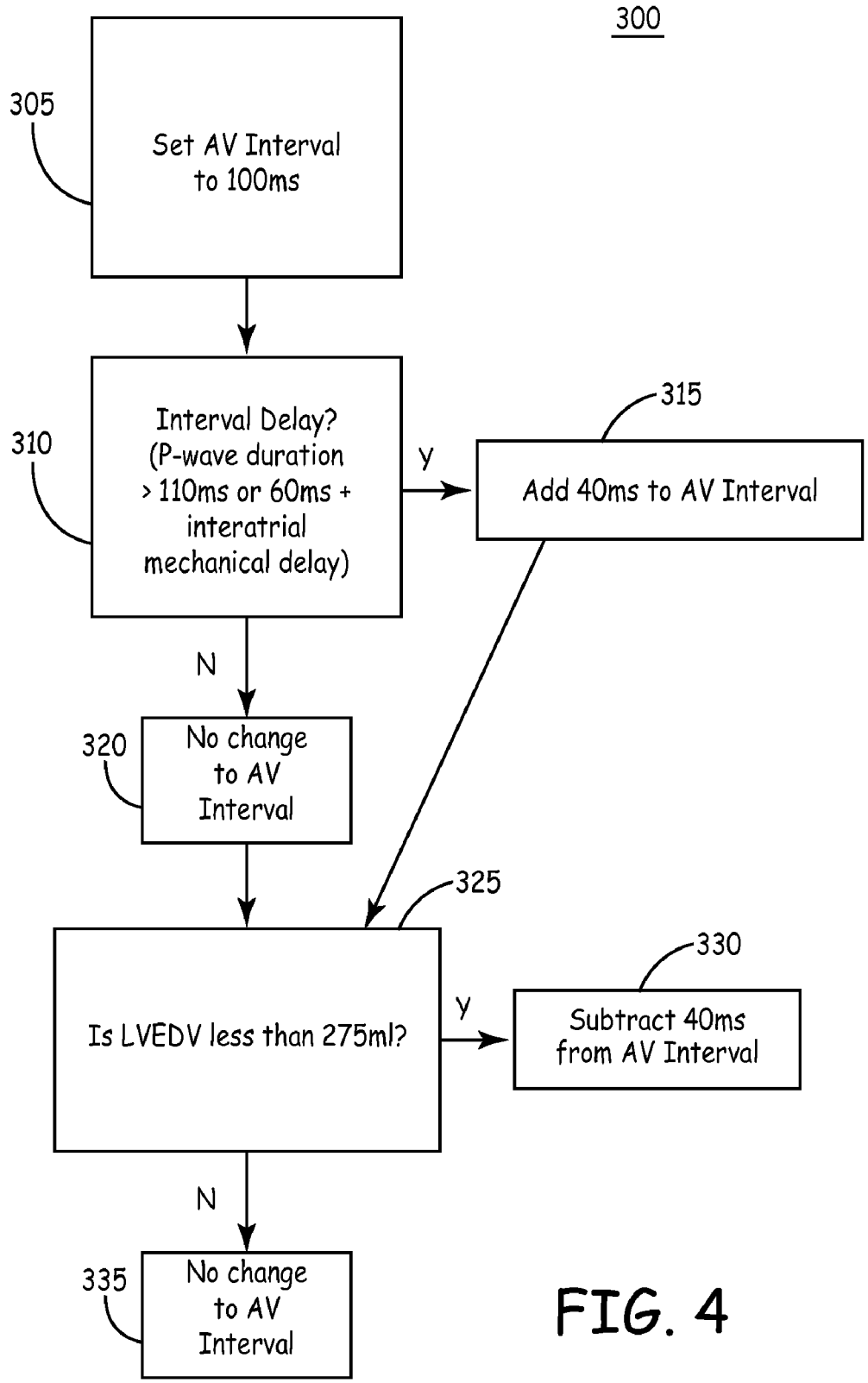
FIG. 4 is a flow chart summarizing steps included in a method for determining an optimal A-V interval.

FIG. 4 is a flow chart summarizing steps included in a method for determining an optimal A-V interval for use in method 200 of FIG. 3. Method 300 begins at step 305 by setting the A-V interval to a desired nominal value. For example, a nominal A-V interval setting of 100 ms may be used. At step 310, any intra-atrial delay present is monitored and characterized using, for example, non-invasive echocardiographic equipment, surface-based EGG equipment and/or internal electrogram (EGM) monitoring techniques. For example, in the embodiment depicted at FIG. 4, inter-atrial delay is declared present if a P-wave duration exceeds about 100 ms or the RA activates more than 60 ms prior to the LA activation. However, other values and techniques may be used. As depicted in FIG. 4, in the event that inter-atrial delay is deemed present, then at step 315 the A-V interval is incremented upward (as depicted 40 ms is added to the A-V interval). If no inter-atrial delay is present then at step 320 no change to the A-V interval occurs and the method proceeds to step 325. At step 325, an LVEDV value is obtained (e.g., measured or otherwise determined). If the LVEDV value exceeds a threshold value (i.e., 275 ml as shown in FIG. 4), then at step 330 the A-V interval is decremented by an amount (e.g., 40 ins). If the LVEDV value does not exceed the threshold value, then at step 335 no change is made. Also, a different or additional initial A-V interval may be used than the 100 ms value described above. In addition, the method depicted in FIG. 4 may be iteratively applied, periodically or otherwise anytime that one or more of LVEDV, LVESV and/or inter-atrial delay information is available for a given patient. Furthermore, one or more mechanical sensors may be used to confirm that physiologically appropriate A-V intervals are being used.

In a patient with intact atrioventricular conduction, the method depicted and described with respect to FIG. 4 may include patient's intrinsic A-V interval as a factor in setting the initial A-V interval (at step 305). This may be very useful in the event that the patient is receiving so-called fusion pacing based on intrinsic atrial activation. In order to allow intrinsic A-V conduction, the A-V interval is set at a maximum setting or a setting longer than the intrinsic A-V conduction time. The intrinsic A-V conduction time may be determined by measuring the interval from an atrial pacing pulse to a subsequently sensed R-wave. Remaining test A-V intervals may be applied at decreasing increments from the intrinsic A-V interval. Alternatively, test A-V intervals may be applied randomly ranging from 0 ms to the intrinsic A-V interval. If atrioventricular conduction is not intact, a set of test A-V intervals may be selected over a predefined range, for example a range from 0 ms to on the order of 250 ms.

While not depicted, sustaining a stable heart rate during the data acquisition interval is performed may be beneficial. Heart rate instability, such as the presence of ectopic heart beats or other irregularities, can produce anomalous mechanical (motion) data. As such, the heart rate preferably stays within a specified range. In one embodiment, heart rate stability may be verified by determining the average and standard deviation of the cardiac cycle length during the data acquisition period. The cardiac cycle length may be determined as the interval between consecutive ventricular events including ventricular pacing pulses and any sensed R-waves. If the average cardiac cycle length or its standard deviation falls outside a predefined range, the data is considered unreliable.

When method 300 is executed by an external pacing system, the obtained data relating to LVEDV, LVESV and/or inter-atrial (electrical or mechanical) delays may be displayed in real-time or stored and presented following an optimization procedure. When method 300 for identifying an optimal A-V interval is executed by an implanted device, the obtained data may be stored for later uplinking to an external device for display and review by a physician.

The optional steps 220,225,230 of FIG. 3 for determining an optimal V-V interval are now briefly described. The optimal A-V interval is programmed to an optimal setting determined according to method 300 of FIG. 4. The V-V interval is set to a test interval and a range of test intervals are predefined and may be delivered in a random, generally increasing, or generally decreasing fashion. A range of test intervals may include intervals that result in the right ventricle being paced prior to the left ventricle and intervals that result in the left ventricle being paced prior to the right ventricle. A set of exemplary test intervals includes right ventricular pacing 20 ms and 40 ms prior to left ventricular pacing, simultaneous left and right ventricular pacing (a V-V interval of 0 ms), and left ventricular pacing 20 ms and 40 ms prior to the right ventricle. After each of a plurality of test V-V intervals are applied, the optimal V-V interval is identified as having the least amount of extraneous or dyssynchronous motion. When the V-V interval is determined using an external pacing system in a clinic having echocardiographic imaging and measurement equipment, ventricular volumes, ventricular wall motion and/or septal wall motion data may be displayed in real-time or stored and presented during optimization procedures. When identifying an optimal V-V interval using an implanted device, the volume data and/or wall motion data may be stored for later uplinking to an external device for display and review by a physician. After identifying the optimal V-V interval, the V-V interval setting may be automatically adjusted or programmed.

When the methods of the present invention are implemented in an implantable device, stored data available through uplink telemetry to an external device can be displayed and/or reviewed by a physician. When such methods are implemented in an external device, a display of cardiac function data may be updated periodically as an intra- or inter-atrial delay characteristic changes.

Thus, a method and apparatus have been described for optimizing a cardiac therapy. The methods described herein may advantageously be applied in numerous cardiac monitoring or therapy modalities including chronic or acute applications associated with implantable or external devices. In addition, certain of the methods and apparatus operated according to the present invention can be operated using computer processors operating pursuant to instructions stored on a computer readable medium.

The invention claimed is:

1. A system for providing optimized cardiac chamber resynchronization therapy (CRT) to a patient, comprising:
   means for obtaining at least one of an inter-atrial delay value and an intra-atrial delay value for a subject; and
   means for utilizing the at least one of the inter-atrial delay value and the intra-atrial delay value to set an operative atrio-ventricular (A-V) delay that enhances the hemodynamic effects of the CRT delivery.

2. A system according to claim 1 further comprising:
   means for programming a cardiac pacing therapy which includes the operative A-V delay.

3. A system according to claim 1, wherein the means for obtaining includes at least one of an echocardiographic apparatus and an electrocardiogram apparatus.

4. A system according to claim 1, wherein the means for obtaining comprises a pair of electrodes adapted to be disposed in operative electrical communication with the atrial chambers of a heart.

5. A system according to claim 1, wherein the obtaining means for comprises means for measuring P-wave width.

6. A method for providing optimized cardiac chamber resynchronization therapy (CRT) to a patient, comprising:
   obtaining at least one of an inter-atrial delay value and an intra-atrial delay value of a patient; and
   programming an operative A-V delay delay correlated to the at least one of the inter-atrial delay value and the intra-atrial delay value and to enhance the hemodynamic effects of the CRT delivery.

7. A method according to claim 6, further comprising:
   programming a inter-ventricular (V-V) pacing delay that corresponds to the operative A-V delay delay.

8. A method according to claim 6, wherein the obtaining step is performed using one of an electrocardiogram apparatus and an echocardiographic apparatus.

9. A method according to claim 6, wherein the obtaining step comprises employing a pair of electrodes disposed in operative electrical communication with at least one of the atria of the patient's heart.

10. A method according to claim 6, wherein the obtaining step comprises measuring P-wave width.

11. A computer readable medium for storing executable instructions for providing optimized cardiac chamber synchronization to a patient during delivery of a cardiac pacing therapy, comprising:
   instructions encoded into a computer readable medium for obtaining at least one of an inter-atrial delay metric and an intra-atrial delay metric; and
   instructions encoded into the computer readable medium for correlating the at least one of the inter-atrial delay metric and the intra-atrial delay metric to a physiologically optimized atrio-ventricular (A-V) delay to enhance the hemodynamic effects of the CRT delivery.

12. A medium according to claim 11, further comprising:
   instructions encoded into the computer readable medium for programming a cardiac pacing therapy utilizing the operative A-V delay delay.

13. A medium according to claim 11, wherein the instructions for obtaining comprise instructions for obtaining P-wave width.

14. A method or providing optimized cardiac chamber resynchronization therapy (CRT) to a patient using a cardiac pacemaker, comprising:
   delivering cardiac pacing using an initial A-V delay delay;
   measuring an inter-atrial delay during the pacing delivered using the initial A-V delay delay;
   comparing the inter-atrial delay to a predetermined threshold; and
   programming the pacemaker to employ an operative A-V delay delay incremented from the initial A-V delay delay in response to the inter-atrial delay exceeding the threshold and the programming the pacemaker to employ an operative A-V delay delay unchanged from the initial A-V delay delay in response to the inter-atrial delay not exceeding the threshold.

15. The method of claim 14 wherein measuring the inter-atrial delay comprises measuring P-wave duration.

16. The method of claim 14 further comprising:
   delivering the CRT using the operative A-V delay delay;
   measuring a left ventricular end diastolic volume (LVEDV) during the CRT using the operative A-V delay delay;
   comparing the LVEDV to a predetermined value; and
   programming a next operative A-V delay delay to a decremented delay from the operative A-V delay delay in response to the LVEDV exceeding the threshold value and leaving the operative A-V delay delay unchanged if the LVEDV does not exceed the threshold value.

* * * * *